United States Patent [19]

Hagen

[11] Patent Number: 5,856,592

[45] Date of Patent: Jan. 5, 1999

[54] CONTINUOUS VAPOR PHASE PROCESS FOR DIRECT CONVERSION OF METHANOL TO HIGHER ALCOHOLS

[75] Inventor: Gary P. Hagen, West Chicago, Ill.

[73] Assignee: Amoco Corporation, Chicago, Ill.

Related U.S. Application Data

[60] Provisional application No. 60/021,322, Jul. 8, 1996.

[21] Appl. No.: 834,985

[22] Filed: Apr. 7, 1997

[51] Int. Cl.$^6$ ..................................................... C07C 27/00
[52] U.S. Cl. ........................................ 568/902.2; 568/904
[58] Field of Search .................................. 568/902.2, 904

[56] References Cited

U.S. PATENT DOCUMENTS

5,095,156   3/1992   Radlowski ............................... 568/905
5,159,125  10/1992   Hagen ..................................... 568/904

*Primary Examiner*—Gary Geist
*Assistant Examiner*—Jean Vollano
*Attorney, Agent, or Firm*—Thomas A. Yassen; Robert E. Sloat

[57] ABSTRACT

A continuous vapor phase processes for direct condensation of methanol and/or dimethyl ether with dilute acetylene feedstream to a mixture containing at least one higher molecular weight alkanol, such as n-propanol or isobutanol, over an alkaline catalyst which is, advantageously, an essentially magnesium oxide catalyst.

17 Claims, 3 Drawing Sheets

5,856,592

CONTINUOUS VAPOR PHASE PROCESS FOR DIRECT CONVERSION OF METHANOL TO HIGHER ALCOHOLS

CROSS-REFERENCE TO RELATED APPLICATION

This application claims the benefit of U.S. Provisional application No. 60/021,322, filed Jul. 8, 1996, which application is specifically incorporated herein, in its entirety, by reference.

TECHNICAL FIELD

The present invention relates to a continuous vapor phase process for direct catalytic conversion of methanol to a mixture containing at least one higher molecular weight alkanol over an alkaline catalyst. More specifically, it relates to continuous vapor phase processes for direct condensation of methanol and/or dimethyl ether with dilute acetylene feedstream to a mixture containing at least one higher molecular weight alkanol, such as n-propanol or i-butanol, over an alkaline catalyst which is, advantageously, an essentially magnesium oxide catalyst.

In another aspect this invention relates to a vapor phase process for upgrading of dilute acetylene-containing feedstreams by conversion of acetylene with one or more lower molecular weight alcohols or their dehydration products, e.g., alkenes, optionally in combination with a lower molecular weight aldehyde and/or ether, to a mixture containing at least one higher molecular weight alkanol over an alkaline catalyst which is, advantageously, an essentially magnesium oxide.

BACKGROUND OF THE INVENTION

In recent years there has been an upsurge in interest in the production of both chemicals and transportation fuels from non-petroleum carbon sources such as methane, tar sands, oil shale and the like. This interest has focused for lack of good direct conversion processes on indirect processes, which often go through a synthesis gas intermediate with subsequent conversion of the synthesis gas via Fischer-Tropsch and related processes to hydrocarbons and/or oxygenates. Oxygenates, particularly lower alkanols, are common products of such synthesis gas reactions, and high conversion, selective processes to convert an alkanol or a mixture of alkanols to higher molecular weight alkanols have substantial commercial potential.

One potential process for alkanol feeds uses the well-known, non-catalytic Guerbet reaction which converts a lower molecular weight alkanol to a branched or linear higher molecular weight alkanol in the presence of an alkali metal alkoxide dissolved in the alkanol to be converted. Such processes are uncatalyzed, moderate temperature batch reactions. When considered for industrial use, however, the Guerbet reaction suffers an economic disadvantage in that a portion of the starting alkanol (and possibly some of the product) is consumed by oxidation to the corresponding carboxylic acid unless special agents are added. One publication suggests the use of a mixture of potassium hydroxide and boric oxide to suppress acid formation which is said to improve the yield.

More recently, an improved Guerbet reaction has been reported which uses a "catalyst" system employing magnesium oxide, potassium carbonate, and copper chromite for converting, for example, ethanol to higher alcohols including 1-butanol, and 1-butanol to higher alkanols including 2-ethyl-1-hexanol (J. Org. Chem. 22, 540–2 (1957)). The reaction is of the batch type and the "catalyst" is said to have limited lifetime.

Another improvement in the Guerbet reaction, discussed in J. Mol. Catalysis 33, 15–21 (1985), uses a sodium alkoxide mixed with 5 percent rhodium on alumina as a "catalyst." Mixtures of 1-butanol and methanol are said to be converted by the "catalyst" to a mixture of 2-ethyl-1-hexanol and 2-methyl-1-butanol.

Still other batch Guerbet reaction variations include water removal to improve yield and the use of an alkali metal hydroxide "catalyst" (U.S. Pat. No. 3,328,470), the use of an alkali metal alcoholate/boric acid ester "catalyst" (U.S. Pat. No. 2,861,110), and the addition of a nickel "catalyst" to the metal alkoxide (J. Am. Chem. Soc. 7 & 52 (1953)).

Octane demand has continued to increase in recent years and growth is likely to continue in the United States. For example, it has been estimated that clear pool octane demand has been increasing by 0.15 units/year in recent years. Addition of alkanols and ethers such as methanol, ethanol and methyl t-butyl ether to gasoline to improve octane number and/or improve the effect of gasoline combustion in internal combustion engines on the environment has been the subject of a number of recent publications.

Methanol is generally made from synthesis gas and ethanol can be made by carbonylation of methanol or more usually from agricultural products by fermentation. Higher alkanols can also result from the catalyzed conversion of synthesis gas. Olefins such as ethylene and propylene are made in large quantities by the cracking of alkanes such as ethane, propane and naphtha. Potentially, additional large amounts of ethylene are available from natural gas by the oxidative coupling of the methane component.

Methanol, while effective if used essentially pure for transportation fuel, is not a good additive for gasoline and is also potentially available in large quantities by the partial oxidation the methane component in natural gas. Ethanol has shown promise as a gasoline additive, but isobutanol in particular is valuable as it can be dehydrated to isobutylene and reacted with methanol to form methyl t-butyl ether which is an excellent octane improver that can be easily blended into gasoline. Isobutanol is also an effective octane improver. The methyl ether of i-pentanol is also an excellent octane improver for gasoline. U.K. Patent Application GB 2,123,411 describes a process for making a mixture of octane improving ethers by synthesizing an alkanol mixture containing methanol, ethanol, and higher alkanols and dehydrating the higher alkanols and etherification.

Because of the large amount of methanol available and its problems as a gasoline additive, processes which convert methanol to effective gasoline additives are valuable. Well-known is the Mobil process for converting methanol to gasoline-range hydrocarbons over an aluminum-containing molecular sieve. Little work has been reported on effectively converting methanol to higher alcohols, in particular, i-butanol.

Now a process has been found which allows a continuous, vapor phase, catalytic Guerbet-type of condensation to be effected on a large variety of different alkanols, their dehydration products (alkenes), aldehydes, ethers and mixtures thereof. In particular, a continuous vapor phase process for direct condensation of methanol and/or dimethyl ether with dilute acetylene feedstream to form a mixture containing at least one higher molecular weight alkanol, such as n-propanol or i-butanol, over an alkaline catalyst which is, advantageously, an essentially magnesium oxide catalyst.

SUMMARY OF THE INVENTION

Economical processes are disclosed for conversion of methanol and/or dimethyl ether with dilute acetylene feedstream in the vapor phase over an alkaline catalyst which is, advantageously, magnesium oxide, to form a mixture containing at least one higher molecular weight alkanol, such as n-propanol or i-butanol.

In one embodiment the invention is a continuous vapor phase process for direct catalytic conversion of methanol in combination with dilute acetylene-containing feedstream to at least one higher molecular weight alkanol which comprises contacting the dilute acetylene-containing feedstream and methanol in the vapor phase with a catalyst which is at least one oxide of a metal selected from Group IIA in the Periodic Table of Chemical Elements, under condensation conditions to form a mixture containing at least one higher molecular weight alkanol. The Periodic Table of Chemical Elements showing Group IIA is published, e.g., in "Webster's Ninth New Collegiate Dictionary" page 874 (Merrian-Webster Inc., 1984). One preferred catalyst for conversions according to the invention is essentially magnesium oxide.

In another embodiment the invention is a continuous vapor phase process direct catalytic conversion of methanol in combination with dilute acetylene-containing feedstream comprising acetylene and one or more $C_3$ or higher alkynes in combination with methanol to at least one higher molecular weight alkanol which comprises contacting methanol and the feedstream in the vapor phase with a catalyst which is essentially magnesium oxide under condensation conditions to form a mixture containing said at least one or more higher molecular weight alkanol.

In yet another embodiment the invention is a continuous vapor phase process for direct catalytic conversion methanol in combination with dilute acetylene-containing feedstream to at least one higher molecular weight alcohol which comprises contacting the dilute acetylene-containing feedstream and methanol in the vapor phase with a catalyst which is essentially magnesium oxide containing a low loading of an oxide selected from the group consisting of aluminum, zinc and zirconium, under condensation conditions to form a mixture containing at least one higher molecular weight alcohol.

BRIEF DESCRIPTION OF THE DRAWINGS

For a more complete understanding of the present invention, reference should now be made to the embodiments illustrated in greater detail in the accompanying drawings and described below by way of examples of the invention.

GENERAL DESCRIPTION OF THE INVENTION

According to the invention there is provided a reactor system and process which can economically and efficiently convert methanol in combination with dilute acetylene-containing feedstream to at least one higher molecular weight alkanol in a vapor phase, essentially isobaric plug-flow reactor, which reactor contains a fixed-bed, subfluidized stirred-bed, or fluidized-bed of heterogeneous catalyst capable of multiple temperature operation.

The $C_2$ or higher alcohols useful herein are $C_2$ to $C_{20}$ alcohols such as ethanol, a propanol, a butanol, a pentanol, a hexanol, a nonanol, a dodecanol, and the like. The only limitation on such alcohols is their ability to be vaporized and passed over the catalyst at a temperature low enough to avoid substantial decomposition. The $C_2$ or higher alkynes useful herein are $C_2$ to $C_{12}$ olefins such as ethyne, propyne, 1- and 2-pentyne, 1-penten-3-yne, 2,5-dimethyl-3-hexyne etc. Preferably the $C_2$ or higher alkyne is ethyne, or propyne. Most preferably, it is ethyne. Such feeds can also contain one or more $C_1$ to $C_4$ aldehydes or one or more $C_1$ to $C_6$ ethers.

Suitable $C_1$ to $C_4$ aldehydes and $C_1$ to $C_6$ ethers generally include aldehydes and ethers such as formaldehyde, acetaldehyde, propionaldehyde, dimethyl ether, diethyl ether, methyl ethyl ether, methyl isopropyl ether, and the like. An especially preferred feed is a mixture of methanol, ethylene, and acetaldehyde, a mixture of methanol and ethylene, a mixture of methanol, ethylene, and propylene, or a partially separated effluent from a olefins unit combined with methanol. Feed to processes of this invention may, additionally, contain amounts of one or more of methane, oxygen, nitrogen, hydrogen, carbon monoxide and carbon dioxide.

In general, after the feedstream is passed over the catalyst it will contain a mixture of alcohols at least one of which is of higher molecular weight than any of the starting alcohol or olefin. For example, a mixture of methanol and ethanol and a mixture of methanol, formaldehyde and ethanol produces at least 1-propanol, and a mixture of methanol, ethanol, and 1-propanol produces at least isobutanol; a mixture of methanol and isopropanol produces at least 2-butanol; ethanol alone produces at least n-butanol; n-butanol alone produces at least 2-ethylhexanol, and propanol alone produces at least 2-methylpentanol. Small amounts of non-alcohol products such as aldehydes, ethers and ketones generally also occur in the product.

A mixture of methanol and ethylene produces n-propanol, i-butyl alcohol and isomeric $C_4$ aldehydes, and a mixture of methanol and propylene produces similar products.

The magnesium oxide component useful in the catalyst herein described is essentially magnesium oxide. The magnesium oxide is present as more than about 80, more preferably more than about 90, and most preferably, more than about 95 weight percent of the total catalyst weight. The catalyst may also contain minor amounts of magnesium hydroxide, or alkaline materials such as a Period Group IA or Group IIA compound including oxides and hydroxides. The magnesium oxide component is preferably of higher surface area, including an areas of up to 300 square meters per gram ($M^2$/g) and higher, more preferably of surface area greater than about 25 $M^2$/g, and most preferably, of surface area above about 50 $M^2$/g, as measured by the BET method with nitrogen.

Magnesium oxide for use according to the invention can be made by calcination of magnesium hydroxide or another magnesium compound such as magnesium carbonate or acetate. Preferred magnesium compounds include magnesium hydroxide. Calcination temperature of the magnesium compound used should not be greatly in excess of the temperature needed to produce the oxide as the oxide can be produced in a less active form.

Catalyst may be used neat, but can be admixed with a diluent such as zinc oxide, zirconia, titania, boria, alumina, and, particularly, a carbonaceous material such as charcoal and the like. Such diluents need not be completely inert and, indeed, it appears that the use of charcoal as a diluent improves certain of the condensation reactions described herein such as that of a mixture of methanol and ethanol, a mixture of methanol, ethanol and a propanol, and a mixture of acetylene and methaol or dimethyl ether. The diluent and the magnesium oxide component may be admixed in proportions of from 100 weight percent magnesium oxide component and no diluent to about 10 weight percent magnesium oxide component and about 90 weight percent diluent. More preferably, the proportions may vary between about 80 weight percent magnesium oxide component and about 20 weight percent diluent to about 20 weight percent magnesium oxide component and about 30 weight percent diluent. Alternatively, lesser amounts of diluent oxides may be supported on or incorporate into magnesium oxide.

The magnesium oxide component may in addition be supported on such supports as titania, alumina, silica, boria, zinc oxide, zirconia, and a carbonaceous material such as charcoal and the like, by impregnation or otherwise. Magnesium oxide component-support weight percent ratios are generally the same as described above for catalysts wherein the magnesium oxide component is admixed with a diluent.

Use of a carrier gas mixed with the feed to the process can be advantageous. Such materials as hydrogen, carbon monoxide, carbon dioxide, a hydrocarbon, and inert gases such as nitrogen, argon, and the like may be used to improve the condensation reaction. The use of hydrogen in the process can improve selectivity in the reaction of methanol with another alcohol and, if used, is generally employed in a hydrogen/feed ratio of from about 20:1 to about 1:1, more preferably, about from 10:1 to about 1:1.

The catalyst, with or without a carrier gas added to the feed, can be used in a fixed bed, ebullated bed, fluidized bed, or other type of vapor phase process. A copper-walled reactor has been found to be beneficial. In general, the temperature range useful in carrying out the condensation reaction described herein runs between about 300° and about 700° C., more preferably, between about 300° and about 500° C., and most preferably, between about 325° and about 475° C. The range of total reactor pressure useful in this invention runs between sub-atmospheric and about 1000 psig, more preferably, between sub-atmospheric and about 600 psig, and most preferably, sub-atmospheric to about 500 psig. Useful weight hour space velocities run between about 0.05 and about 60 $hr^{-1}$, and more preferably, between about 0.05 and about 10 $hr^{-1}$, based upon the magnesium oxide component in the catalyst.

A particularly useful process, when carried out in accordance with the invention, is the production of a mixture rich in n-propanol and i-butanol, from methanol and synthesis gas containing up to about 15 mole percent acetylene. Other catalysts may also be used. The n-propanol and i-butanol, may then be separated from the mixture, dehydrated, and reacted with additional methanol to form higher molecular weight oxygen-containing organic compounds.

DESCRIPTION OF THE PREFERRED EMBODIMENTS

In view of the features and advantages of the continuous vapor phase processes for direct condensation of methanol and/or dimethyl ether with dilute acetylene feedstream to a mixture containing at least one higher molecular weight alcohol in accordance with this invention as compared to the known methanol condensation systems previously used, the following example is given.

EXAMPLES

General

Mixtures of alcohols were evaluated in a fixed bed, continuous, down flow, stainless steel reactor. For some of the studies the stainless steel reactor was equipped with either a quartz or a copper liner. The catalyst was ground to 12/20-mesh size and physically mixed with bed diluent, charcoal, or alumina of the same mesh size. The catalyst bed was centered in the reactor with an inert alumina balls baffle above and below it for improved heat transfer. The alumina balls were kept at a lower temperature than the catalyst bed. The unit was pressured with helium unless otherwise noted and the catalyst brought to reaction temperature in flowing helium, at which time the alcohol was introduced via a Ruska pump.

Products were analyzed by three gas chromatographic systems. The fixed gases, carbon monoxide and carbon dioxide along with $CH_4$ were analyzed by an on-line Hewlett-Packard 5730 gas chromatograph equipped with a thermal conductivity detector and a Chromosorb 106 packed column. Analysis was accomplished by using an external standard calibrated for carbon monoxide, carbon dioxide and methane. The non-condensable light gases, $C_1$ to $C_6$, were analyzed off-line using a flame ionization detector and a 6 ft N-octane Porosil C column. The peaks were identified and measured by matching retention times with an external standard containing $C_1$ to $C_6$ hydrocarbons.

Condensable materials were collected in a bomb and analyzed with a flame ionization detector equipped with a 30 m capillary column of fused silica containing RSL 160 liquid phases. Peaks were identified by matching retention times of known alcohols, aldehydes, esters, ketones, olefins and paraffins. Many smaller peaks were not identified. The results are expressed in relative weight percents.

Condensable liquids were also measured on a Hewlett-Packard 5730 gas chromatograph equipped with a thermal conductivity detector. A 6 ft×⅛ in Poropak QS column, 80/100 mesh particles, was used. This system gave semi-quantitative results for water, $C_1$ to $C_6$ alcohols, and some of the lower molecular weight aldehydes, ketones and esters.

In all cases methanol and/or other liquid reactants were metered by use of a syringe pump into a preheat zone of a quartz micro reactor which was electrically heated and operated at atmospheric pressure. Ethylene or nitrogen carrier gas was metered into the top of the downflow reactor by use of Brooks Mass-flow Controllers. Liquid product was collected in a U-tube receiver chilled to −78° C. with a dry-ice isopropyl alcohol cooling bath in most cases or to 0° C. with an ice bath during those cuts when a gas sample was being taken. In all cases, the catalyst volume was 9.4 cc.

Magnesium oxide catalyst was prepared by drying and calcination of 450° C. of firm homogeneous paste prepared from commercial magnesium hydroxide and distilled water. Additional catalyst components were incorporated into the paste either as solid hydroxides or soluble salts.

Example 1

Magnesium oxide was prepared from 25 kg of commercially available magnesium hydroxide (VWR Scientific, Inc. reagent grade powder) by first mixing with 2000 g of distilled water and extruding the mass through a ⅛ in die plate. The extrudate was dried overnight at 120° C. and calcined first at 300° C. for 1 hr and then 450° C. for 12 hr. The resulting MgO having a BET surface area of 29 $M^2/g$ was used for the following examples.

Example 2

Figure 1:
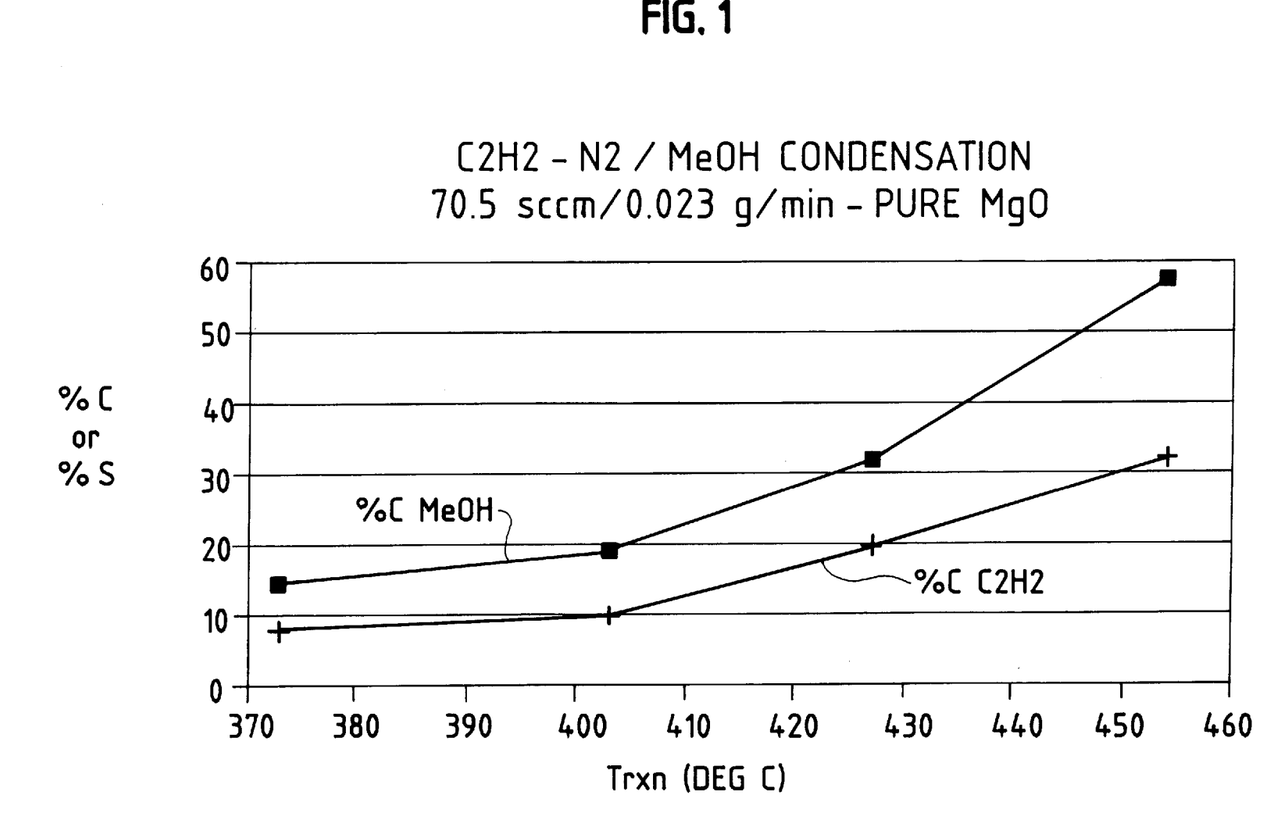
FIG. 1, FIG. 2, and FIG. 3 are graphical depictions of experimental results from a preferred example of the present invention for direct condensation of methanol with dilute acetylene feedstream to a mixture containing higher molecular weight alkanols, such as ethanol, n-propanol and i-butanol, over an alkaline catalyst which is, essentially, magnesium oxide.

Magnesium oxide catalyst prepared as in Example 1 was tested for condensation of feedstream consisting of methanol (0.023 g/min MeOH), and acetylene/nitrogen (70.5 ccm $C_2H_2/N_2$) at temperatures from 373° C. to 454° C. and ambient pressure. At reaction temperature of 454° C. reactant conversions were; 31.89 percent for acetylene, and 57.25 percent for methanol. Results at several temperatures are given below in Table I and in FIG. 1.

Example 3

Figure 2:
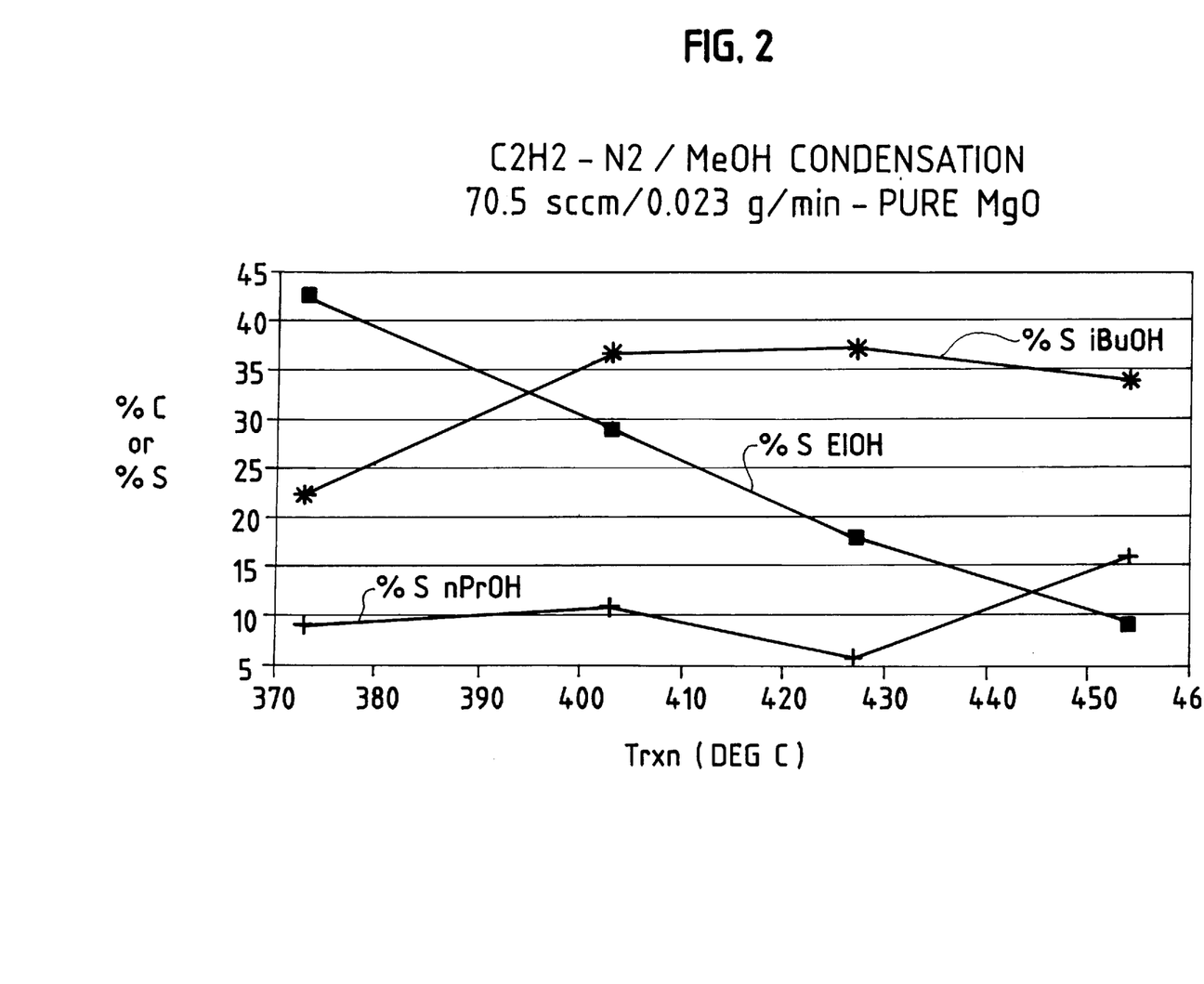
Figure 3:
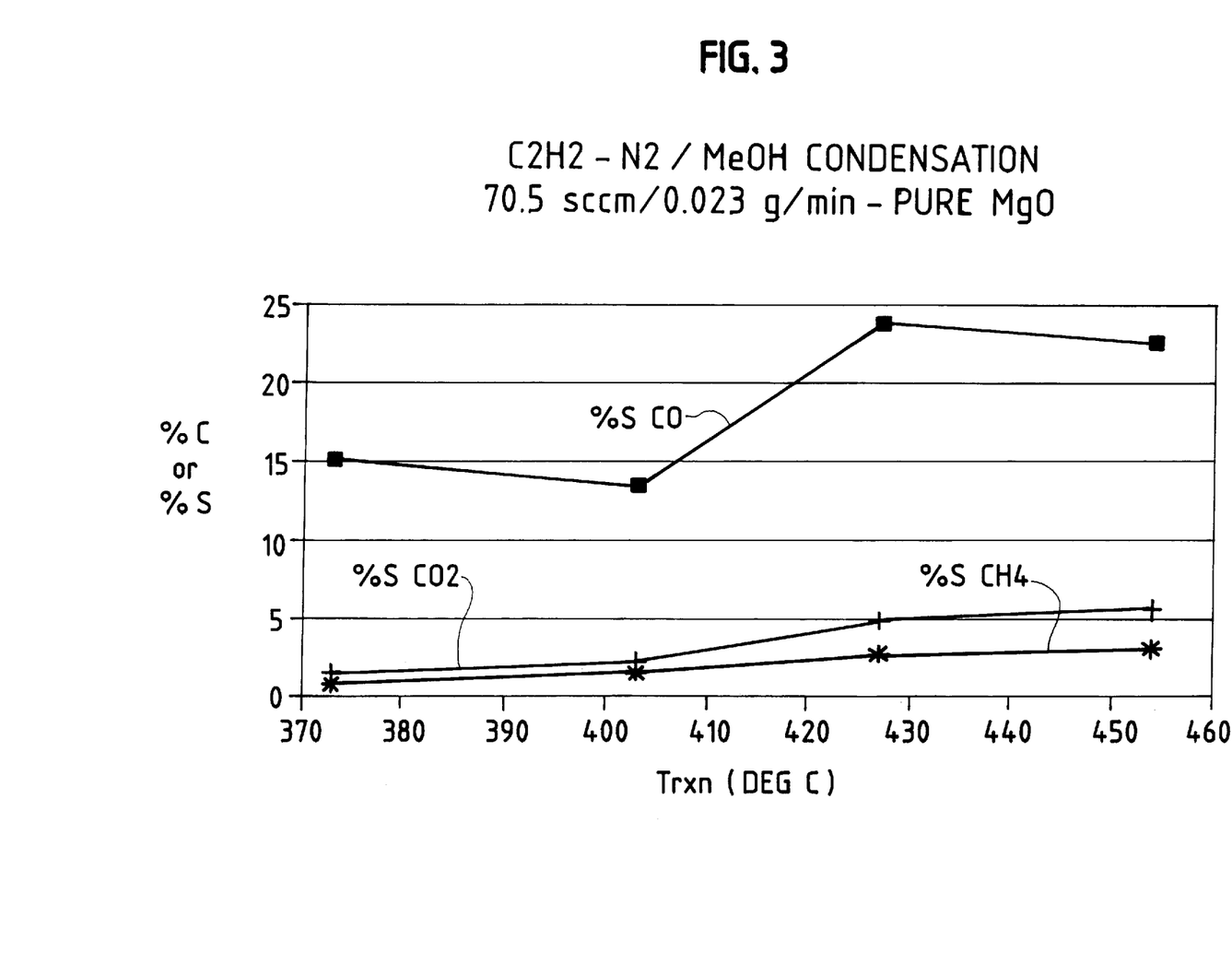

Magnesium oxide catalyst prepared as in Example 1 and treated to provide an aluminum oxide loading of 1 weight percent was tested for condensation of feedstream consisting of methanol (0.01 g/min MeOH), dimethyl ether (6.47 ccm DME), and acetylene/nitrogen (69.67 ccm $C_2H_2/N_2$) at temperatures from 376° C. to 450° C. and ambient pressure. At reaction temperature of 429° C reactant conversions were; 11 percent for diethyl ether, 14.5 percent for acetylene, and 23.9 percent for methanol. Results at several temperatures are given below in Table II and in FIG. 2.

Example 4

A 5/1 methyl alcohol to diethyl ether mixture (0.0126 mL/min of mixture, 6 mL/min of nitrogen) was passed over 9.4 mL of catalyst in a quartz reactor at 430° C. and ambient pressure for 140 min giving 0.94 g of liquid product in a dry ice-isopropanol trap. The product distribution is given below in Table III.

Example 5

Magnesium oxide catalyst prepared as in Example 1 and treated to provide a zirconium oxide loading of 2.4 weight percent was tested for condensation of feedstream consisting of methanol (0.02139 g/min MeOH), and acetylene/nitrogen (69.3 ccm $C_2H_2/N_2$) at temperatures from 374° C. to 454° C. and ambient pressure. The primary alcohol product was isobutyl alcohol. Results at several temperatures are given below in Table V.

Example 6

Magnesium oxide catalyst prepared as in Example 1 and treated to provide an aluminum oxide loading of 1 weight percent was tested for condensation of feedstream consisting of methanol (0.02 g/min MeOH),and acetylene/nitrogen (70.5 ccm $C_2H_2/N_2$) at temperatures from 375° C. to 456° C. and ambient pressure. At reaction temperature of 456° C. reactant conversions were; 30.34 percent for acetylene, and 55.54 percent for methanol. Results at several temperatures are given below in Table VI.

Example 7

Magnesium oxide catalyst prepared as in Example 1 and treated to provide an aluminum oxide loading of 1 weight percent was tested for condensation of feedstream consisting of methanol (0.01 g/min MeOH), dimethyl ether (6.47 ccm DME), and acetylene/nitrogen (69.67 ccm $C_2H_2/N_2$) at temperatures from 376° C. to 450° C. and ambient pressure. At reaction temperature of $_{450}$° C. reactant conversions were; 5.19 percent for dimethyl ether, 17.84 percent for acetylene, and 32.37 percent for methanol. Results at several temperatures are given below in Table VII.

Example 8

Magnesium oxide catalyst prepared as in Example 1 and treated to provide a zinc oxide loading of 1.6 weight percent was tested for condensation of feedstream consisting of methanol (0.0068 g/min MeOH), dimethyl ether (7 ccm DME), water (0.0014 g/min $H_2O$) and acetylene/nitrogen (72.8 ccm $C_2H_2/N_2$) at temperatures from 375° C. to 453° C. and ambient pressure. At reaction temperature of 453° C. reactant conversions were; negative 2.92 percent for dimethyl ether, 15.84 percent for acetylene, and 77.28 percent for methanol. Results at several temperatures are given below in Table VIII.

TABLE I

Conversation of Methanol and Acetylene Feedstream Using MgO Catalyst

| Temperature °C. | 373.00 | 403.00 | 427.00 | 454.00 |
|---|---|---|---|---|
| Feeds | | | | |
| $C_2H_2/N_2$ sccm | 70.50 | 70.50 | 70.50 | 70.50 |
| MeOH g/m | 0.0230 | 0.0230 | 0.0230 | 0.0230 |
| Conversions, mole percent | | | | |
| MeOH | 14.46 | 18.86 | 31.57 | 57.25 |
| $C_2H_2$ | 7.95 | 9.73 | 19.18 | 31.89 |
| Selectivities, percent Gases | | | | |
| CO | 15.13 | 13.39 | 23.75 | 22.61 |
| $CH_4$ | 0.82 | 1.48 | 2.48 | 2.84 |
| $CO_2$ | 1.50 | 2.15 | 4.60 | 5.44 |
| $C_3H_6$ | 0.21 | 0.29 | 0.66 | 0.98 |
| $C_3H_8$ | 2.15 | 0.29 | 0.85 | 0.31 |
| DME | 4.22 | 1.07 | 1.82 | 0.65 |
| AcAld | 0.00 | 0.00 | 0.00 | 0.00 |
| $C_4$ | 0.00 | 0.53 | 0.57 | 2.18 |
| $C_5$ | 0.18 | 0.19 | 0.51 | 0.68 |
| $C_6$ | 0.43 | 1.94 | 2.62 | 3.90 |
| $C_7+$ | 0.00 | 0.40 | 0.72 | 1.12 |
| MeForm | 0.81 | 0.68 | 0.40 | 0.09 |
| EtOH | 42.34 | 28.99 | 17.71 | 8.95 |
| nPrOH | 9.02 | 10.68 | 5.53 | 15.77 |
| DMOE | 0.00 | 0.00 | 0.00 | 0.00 |
| iBuOH | 22.36 | 36.46 | 36.91 | 33.84 |
| Aromat | 0.83 | 1.46 | 0.88 | 0.65 |

Where AcAld is acetaldehyde, MeForm is methyl fromate, EtOH is ethanol, nPrOH is n-propanol, DMOE is 1,1-dimethoxythane, iBuOH is i-butanol, and Aromat. is aromatic compounds

TABLE II

Conversation of Methanol, Dimethyl ether, and Acetylene Feedstream Using 1 Weight Percent $Al_2O_3$/MgO Catalyst

| Temperature °C. | 376.00 | 401.00 | 429.00 | 450.00 |
|---|---|---|---|---|
| Feeds | | | | |
| $C_2H_2/N_2$ sccm | 69.87 | 69.67 | 69.67 | 69.67 |
| DME sccm | 6.47 | 6.47 | 6.47 | 6.47 |
| MeOH g/m | 0.01 | 0.01 | 10.01 | 0.01 |
| Conversions, mole percent | | | | |
| MeOH | −13.09 | −1.81 | 23.93 | 32.37 |
| DME | 3.68 | 12.83 | 11.00 | 5.19 |
| $C_2H_2$ | 4.00 | 8.13 | 14.45 | 17.84 |
| Selectivities, percent Gases | | | | |
| CO | 25.45 | 21.31 | 14.18 | 19.54 |
| $CH_4$ | 0.00 | 2.75 | 3.73 | 3.47 |
| $CO_2$ | 4.60 | 5.04 | 6.39 | 8.50 |
| $C_2H_4$ | 0.00 | 0.00 | 1.95 | 2.78 |
| $C_3H_6$ | 0.00 | 1.15 | 2.24 | 2.62 |
| $C_3H_8$ | 0.00 | 0.00 | 1.17 | 0.00 |
| AcAld | 0.00 | 0.00 | 0.00 | 3.99 |
| $C_4$ | 0.00 | 0.31 | 1.04 | 1.08 |
| $C_5$ | 0.23 | 2.67 | 3.24 | 3.58 |

TABLE II-continued

Conversation of Methanol, Dimethyl ether, and Acetylene Feedstream
Using 1 Weight Percent $Al_2O_3$/MgO Catalyst

| | | | | |
|---|---|---|---|---|
| $C_6$ | 0.00 | 0.00 | 0.97 | 0.00 |
| $C_7$ | 7.51 | 2.14 | 6.59 | 4.55 |
| Liquids | | | | |
| EtOH | 19.20 | 11.80 | 4.67 | 2.85 |
| nPrOH | 20.30 | 25.81 | 25.91 | 25.27 |
| DMOE | 1.75 | 0.55 | 0.00 | 0.00 |
| iBuOH | 18.52 | 24.82 | 26.80 | 23.09 |
| Aromat. | 2.24 | 1.86 | 1.12 | 0.69 |

Where EtOH is ethanol, nPrOH is n-propanol, DMOE is 1,1-dimethoxyethane, iBuOH is i-butanol, and Aromat. is aromatic compounds

TABLE III

| Liquid Product Component | wt. % |
|---|---|
| methyl ether | 5.79 |
| methyl ethyl ether | 3.62 |
| diethyl ether | 41.7 |
| methyl n-propyl ether | 1.53 |
| methyl isobutyl ether | 2.41 |
| propionaldehyde | 0.67 |
| isobutyraldehyde-acetone | 0.84 |
| methanol | 31.4 |
| ethanol | 4.51 |
| n-propanol | 2.21 |
| isobutanol | 4.62 |
| 2-Me-1-butanol | 0.27 |

Comparative Example A

Various mixtures of olefins and methanol in a $N_2$ stream were passed over magnesium oxide catalysts and the products of the reaction determined as set out above. The magnesium oxide catalysts were made by drying and calcining at 450° C. a firm homogeneous paste prepared from commercial magnesium hydroxide and distilled water. Additional components such as silver metal and alumina.

The catalytic results are shown below in Table IV below. Weight percent yield of the reaction products is equal to weight percent selectivity x the estimated conversion of methanol in weight percent as determined by gas-liquid chromatography. A mixture of water and ethylene over the same catalyst yielded no organic products which is evidence that olefin hydration and then condensation does not occur over magnesium oxide.

TABLE IV

Conversion of Methanol with Ethylene or Propylene over MgO

| Olefin[1] | T. °C. | Conv (Wt. %) | $A^5$ | $B^6$ | $C^7$ | $D^8$ | $E^9$ | $F^{10}$ |
|---|---|---|---|---|---|---|---|---|
| C2 | 425 | 1.22 | 0.03 | | 0.34 | | | |
| | 425 | 1.28 | 0.05 | | 0.54 | | | |
| | 425 | 1.69 | 0.07 | | 0.70 | 0.02 | | |
| | 435 | 3.41 | 0.30 | 0.40 | 2.48 | 0.06 | | |
| | 425 | 4.11 | 0.25 | 0.06 | 3.59 | 0.08 | | |
| $C2^2$ | 425 | 0.85 | 0.05 | | 0.60 | | | |
| | 425 | 1.41 | 0.04 | 0.03 | 0.60 | | | |
| | 425 | 1.46 | 0.04 | 0.03 | 0.60 | | | |
| | 435 | 1.52 | 0.10 | 0.04 | 1.09 | | | |
| $C2^3$ | 425 | 4.84 | 0.50 | 0.07 | 3.70 | 0.05 | | |
| | 425 | 6.93 | 0.05 | 0.09 | 5.65 | 0.09 | | |

TABLE IV-continued

Conversion of Methanol with Ethylene or Propylene over MgO

| Olefin[1] | T. °C. | Conv (Wt. %) | $A^5$ | $B^6$ | $C^7$ | $D^8$ | $E^9$ | $F^{10}$ |
|---|---|---|---|---|---|---|---|---|
| | 435 | 10.68 | 1.05 | 0.11 | 9.08 | 0.14 | | |
| C3 | 435 | 4.59 | 0.11 | | 1.07 | 0.3 | | |
| | 435 | 3.30 | 0.12 | | 1.27 | 0.37 | | |
| | 435 | 4.10 | 0.12 | | 1.30 | 0.37 | | |
| | 435 | 3.50 | 0.12 | | 1.45 | 0.42 | | |
| | 435 | 6.45 | 0.27 | 0.03 | 2.20 | 0.54 | | |
| | 435 | 14.04 | 2.15 | 0.09 | 9.01 | 1.23 | | |
| C3 | 425 | 7.46 | 0.15 | 0.03 | 1.86 | 0.80 | | |
| | 425 | 6.68 | 9.15 | | 1.72 | 0.73 | | |
| | 435 | 7.32 | 0.35 | 0.04 | 3.31 | 1.28 | | |
| $C2^3$ | 425 | 9.38 | 3.54 | 0.11 | 2.24 | 0.18 | | |
| | 425 | 6.62 | 1.05 | 0.22 | 2.46 | 0.21 | | |
| | 425 | 4.44 | 0.56 | 0.17 | 2.06 | 0.16 | | |
| | 435 | 6.76 | 0.77 | 0.20 | 3.71 | 0.28 | | |
| $C2^4$ | 425 | 11.39 | | 0.15 | 0.13 | | 0.19 | 0.16 |
| | 425 | 7.47 | | 0.28 | 0.24 | | 0.11 | 0.20 |
| | 425 | 8.88 | | 0.36 | 0.37 | | 0.13 | 0.20 |
| | 400 | 13.38 | | 0.30 | 0.25 | | 0.16 | 0.14 |

[1] olefin/methanol feed ratio is 2.71/1 for all runs
[2] 5% water in feed
[3] 95% MgO and 5% Ag
[4] 90% MgO and 10% Al2O3
[5] i-C4 aldehyde
[6] n-prOH
[7] i-C4OH
[8] 2-Me-l-BuOH
[9] C2 Aldehyde
[10] ETOH

TABLE V

Conversation of Methanol and Acetylene Feedstream
Using 2.4 Weight Percent $ZrO_2$/MgO Catalyst

| Temperature °C. | 375 | 405 | 430 | 454 |
|---|---|---|---|---|
| Feeds | | | | |
| $C_2H_2/N_2$ sccm | 69.3 | 69.3 | 69.3 | 69.3 |
| MeOH g/m | 0.021 | 0.021 | 0.021 | 0.021 |
| Conversions, mole percent | | | | |
| MeOH | 18.68 | 14.57 | 32.32 | 31.01 |
| $C_2H_2$ | 1.55 | 11.12 | 17.61 | 31.99 |
| Selectivities, percent | | | | |
| Gases | | | | |
| CO | 40.13 | 27.97 | 25.51 | 31.01 |
| $CH_4$ | 1.81 | 1.92 | 5.23 | 4.06 |
| $CO_2$ | 4.00 | 2.43 | 4.55 | 6.24 |
| $C_2H_4$ | 0.00 | 0.00 | 1.17 | 0.00 |
| $C_3H_6$ | 0.73 | 0.72 | 1.64 | 1.78 |
| $C_3H_8$ | 0.00 | 0.93 | 0.48 | 0.30 |
| DME | 20.30 | 15.70 | 12.36 | 8.77 |
| $C_4$ | 0.29 | 0.40 | 0.85 | 1.31 |
| $C_5$ | 0.00 | 0.00 | 0.09 | 0.15 |
| $C_6$ | 0.00 | 0.00 | 0.00 | 0.00 |
| MPE | 0.00 | 0.55 | 1.34 | 1.43 |
| Liquids | | | | |
| MeForm. | 0.00 | 1.23 | 0.44 | 0.14 |
| EtOH | 15.99 | 8.740 | 5.45 | 2.93 |
| nPrOH | 0.00 | 9.63 | 8.67 | 8.91 |
| iBuOH | 16.76 | 30.33 | 32.93 | 33.55 |
| Aromat. | 0.00 | 0.00 | 0.35 | 0.87 |
| MIBE | 2.42 | 0.55 | 0.14 | 0.00 |

Where MeForm. is methyl fromate, EtOH is ethanol, nPrOH is n-propanol, iBuOH is i-butanol, Aromat. is aromatic compounds, and MIBE is methyl isobutyl ether.

TABLE VI

Conversation of Methanol and Acetylene Feedstream
Using 1 Weight Percent $Al_2O_3/MgO$ Catalyst

| Temperature °C. | 375 | 404 | 433 | 456 |
|---|---|---|---|---|
| Feeds | | | | |
| $C_2H_2/N_2$ sccm | 70.5 | 70.5 | 70.5 | 70.5 |
| MeOH g/m | 0.02 | 0.02 | 0.02 | 0.02 |
| Conversions, mole percent | | | | |
| MeOH | 12.58 | 21.08 | 38.84 | 55.54 |
| $C_2H_2$ | 5.84 | 12.16 | 19.87 | 30.34 |
| Selectivities, percent | | | | |
| Gases | | | | |
| CO | 9.08 | 14.95 | 17.26 | 19.57 |
| $CH_4$ | 0.52 | 1.53 | 3.10 | 4.36 |
| $CO_2$ | 1.26 | 1.80 | 3.08 | 4.46 |
| $C_2H_4$ | 0.00 | 0.00 | 1.33 | 2.07 |
| $C_3H_6$ | 0.29 | 0.71 | 1.70 | 2.31 |
| $C_3H_8$ | 0.10 | 0.11 | 0.34 | 0.460 |
| DME | 41.76 | 33.96 | 27.09 | 15.63 |
| $C_4$ | 0.00 | 2.25 | 1.11 | 0.72 |
| $C_5$ | 0.97 | 1.27 | 2.14 | 2.79 |
| $C_6$ | 0.158 | 1.31 | 2.11 | 2.62 |
| $C_7+$ | 0.00 | 0.00 | 0.01 | 3.54 |
| Liquids | | | | |
| MeForm. | 0.24 | 0.17 | 0.00 | 1.06 |
| EtOH | 22.09 | 14.42 | 9.46 | 1.38 |
| nPrOH | 8.47 | 9.13 | 10.74 | 18.52 |
| iBuOH | 14.27 | 17.98 | 19.42 | 19.53 |
| Aromat. | 0.37 | 0.41 | 0.63 | 0.62 |

Where MeForm is methyl fromate, EtOH is ethanol, nPrOH is n-propanol, iBuOH is i-butanol, and Aromat. is aromatic compounds

TABLE VII

Conversation of Dimethyl ether, Methanol and Acetylene Feedstream
Using 1 Weight Percent $Al_2O_3/MgO$ Catalyst

| Temperature °C. | 376 | 401 | 429 | 450 |
|---|---|---|---|---|
| Feeds | | | | |
| $C_2H_2/N_2$ sccm | 69.67 | 69.67 | 69.67 | 69.67 |
| DME | 6.47 | 6.47 | 6.47 | 6.47 |
| MeOH g/m | 0.01 | 0.01 | 0.01 | 0.01 |
| Conversions, mole percent | | | | |
| MeOH | -15.09 | -1.81 | 23.93 | 32.37 |
| DME | 3.68 | 12.83 | 11.00 | 5.19 |
| $C_2H_2$ | 4.00 | 8.13 | 14.45 | 17.84 |
| Selectivities, percent | | | | |
| Gases | | | | |
| CO | 25.45 | 21.31 | 14.18 | 19.54 |
| $CH_4$ | 0.00 | 2.75 | 3.73 | 3.47 |
| $CO_2$ | 4.60 | 5.04 | 6.39 | 6.50 |
| $C_2H_4$ | 0.00 | 0.00 | 1.95 | 2.78 |
| $C_3H_6$ | 0.00 | 1.15 | 2.24 | 2.62 |
| $C_3H_8$ | 0.00 | 0.00 | 1.17 | 0.00 |
| AcAld. | 0.00 | 0.00 | 0.00 | 3.99 |
| $C_4$ | 0.00 | 0.31 | 1.04 | 3.58 |
| $C_5$ | 0.23 | 2.67 | 3.24 | 3.58 |
| $C_6$ | 0.00 | 0.00 | 0.97 | 0.00 |
| $C_7+$ | 7.51 | 2.14 | 6.59 | 4.55 |
| Liquids | | | | |
| EtOH | 19.20 | 11.60 | 4.67 | 2.85 |
| nPrOH | 20.50 | 25.81 | 25.91 | 25.27 |
| DMOE | 1.75 | 0.55 | 0.00 | 0.00 |
| iBuOH | 18.52 | 24.82 | 26.80 | 23.09 |
| Aromat. | 2.24 | 1.86 | 1.12 | 0.69 |

Where EtOH is ethanol, nPrOH is n-propanol, DMOE is 1,1-dimethoxyethane, iBuOH is i-butanol, and Aromat. is aromatic compounds

TABLE VIII

Conversation of Dimethyl ether, Methanol, Water and Acetylene Feedstream
Using 1 Weight Percent ZnO/MgO Catalyst

| Temperature °C. | 375 | 403 | 431 | 453 |
|---|---|---|---|---|
| Feeds | | | | |
| $C_2H_2/N_2$ sccm | 72.8 | 72.8 | 72.8 | 72.8 |
| DME | 7.0 | 7.0 | 7.0 | 7.0 |
| MeOH g/m | 0.0068 | 0.0068 | 0.0068 | 0.0068 |
| MeOH g/m | 0.0014 | 0.0014 | 0.0014 | 0.0014 |
| Conversions, mole percent | | | | |
| MeOH | 8.71 | 4.50 | 39.18 | 77.28 |
| DME | -5.96 | -4.86 | -2.69 | -2.92 |
| $C_2H_2$ | 2.38 | 4.34 | 9.68 | 15.84 |
| Selectivities, percent | | | | |
| Gases | | | | |
| CO | 31.50 | 20.68 | 24.25 | 23.54 |
| $CH_4$ | 0.00 | 1.48 | 1.78 | 2.61 |
| $CO_2$ | 18.07 | 20.68 | 21.43 | 19.40 |
| $C_2H_4$ | 0.00 | 0.00 | 0.00 | 1.02 |
| $C_3H_6$ | 0.00 | 0.71 | 0.93 | 2.85 |
| $C_3H_8$ | 0.00 | 0.00 | 0.59 | 2.63 |
| AcAld. | 10.24 | 4.73 | 3.21 | 3.84 |
| $C_4$ | 0.00 | 0.00 | 0.00 | 0.44 |
| $C_5$ | 0.00 | 0.59 | 0.56 | 0.92 |
| $C_6$ | 0.00 | 0.00 | 0.00 | 0.00 |
| $C_7+$ | 14.55 | 7.03 | 4.34 | 0.89 |
| Liquids | | | | |
| MeOH | 8.71 | 4.50 | 39.18 | 77.28 |
| EtOH | 5.75 | 1.27 | 0.42 | 0.00 |
| nPrOH | 11.03 | 18.96 | 25.10 | 28.27 |
| iBuOH | 7.68 | 21.44 | 16.34 | 12.18 |
| Aromat. | 0.75 | 2.02 | 1.06 | 0.35 |

Where MeOH is methanol, EtOH is ethanol, nPrOH is n-propanol, iBuOH is i-butanol, and Aromat. is aromatic compounds That which is claimed is:

1. A continuous vapor phase process for direct catalytic conversion of methanol in combination with dilute acetylene-containing feedstream to at least one higher molecular weight alcohol which comprises contacting the dilute acetylene-containing feedstream and methanol in the vapor phase with a catalyst which is magnesium oxide admixed with a diluent under condensation conditions to form a mixture containing at least one higher molecular weight alcohol.

2. The process of claim 1 wherein the dilute acetylene-containing feedstream comprises a mixture of acetylene, and a synthesis gas comprising dihydrogen and carbon monoxide, and optionally one or more members of the group consisting of dimethyl ether, formaldehyde, ethylene, and propylene.

3. The process of claim 1 wherein the vapor phase has a composition comprising a mixture of acetylene and methanol, a mixture of acetylene, methanol and dimethyl ether, a mixture of acetylene, methanol and ethylene, a mixture of acetylene, methanol, formaldehyde and ethylene, a mixture of acetylene, methanol, ethylene, and propylene or a mixture of acetylene, methanol and propylene.

4. The process of claim 1 wherein said catalyst which is magnesium oxide additionally contains a member selected from the group consisting of Periodic Group IA and IIA metals and compounds.

5. The process of claim 1 wherein the catalyst is magnesium oxide made by thermal decomposition of magnesium hydroxide, the magnesium oxide exhibits a surface area above 50 sq. m/g.

6. The process of claim 5 wherein the dilute acetylene-containing feedstream comprises a mixture of acetylene, and a synthesis gas comprising dihydrogen and carbon monoxide, and optionally one or more members of the group consisting of dimethyl ether, formaldehyde, ethylene, and propylene.

7. The process of claim 5 wherein the vapor phase has a composition comprising a mixture of acetylene and methanol, a mixture of acetylene, methanol and dimethyl ether, a mixture of acetylene, methanol and ethylene, a mixture of acetylene, methanol, formaldehyde and ethylene, a mixture of acetylene, methanol, ethylene, and propylene or a mixture of acetylene, methanol and propylene.

8. A continuous vapor phase process for direct catalytic conversion of methanol in combination with dilute acetylene-containing feedstream to at least one higher molecular weight alcohol which comprises contacting the dilute acetylene-containing feedstream and methanol in the vapor phase with a catalyst which is magnesium oxide admixed with a diluent and containing a low loading of an oxide selected from the group consisting of aluminum, zinc and zirconium oxides, under condensation conditions to form a mixture containing at least one higher molecular weight alcohol.

9. The process of claim 8 wherein the dilute acetylene-containing feedstream comprises a mixture of acetylene, and a synthesis gas comprising dihydrogen and carbon monoxide, and optionally one or more members of the group consisting of dimethyl ether, formaldehyde, ethylene, and propylene.

10. The process of claim 8 wherein the vapor phase has a composition comprising a mixture of acetylene and methanol, a mixture of acetylene, methanol and dimethyl ether, a mixture of acetylene, methanol and ethylene, a mixture of acetylene, methanol, formaldehyde and ethylene, a mixture of acetylene, methanol, ethylene, and propylene or a mixture of acetylene, methanol and propylene.

11. The process of claim 8 wherein said catalyst which is magnesium oxide additionally contains a member selected from the group consisting of Periodic Group IA and IIA metals and compounds.

12. The process of claim 8 wherein the catalyst is magnesium oxide made by thermal decomposition of magnesium hydroxide, the magnesium oxide exhibits a surface area above 50 sq. m/g.

13. The process of claim 12 wherein the dilute acetylene-containing feedstream comprises a mixture of acetylene, and a synthesis gas comprising dihydrogen and carbon monoxide, and optionally one or more members of the group consisting of dimethyl ether, formaldehyde, ethylene, and propylene.

14. The process of claim 12 wherein the vapor phase has a composition comprising a mixture of acetylene and methanol, a mixture of acetylene, methanol and dimethyl ether, a mixture of acetylene, methanol and ethylene, a mixture of acetylene, methanol, formaldehyde and ethylene, a mixture of acetylene, methanol, ethylene, and propylene or a mixture of acetylene, methanol and propylene.

15. The process of claim 12 wherein the catalyst is magnesium oxide containing from about 0.1 percent up to about 10 percent by weight of aluminum oxide.

16. The process of claim 12 wherein the catalyst is magnesium oxide containing from about 0.1 percent up to about 10 percent by weight of zinc oxide.

17. The e process of claim 12 wherein the catalyst is magnesium oxide containing from about 0.1 percent up to about 10 percent by weight of zirconium oxide.

* * * * *